United States Patent [19]

Blondelle et al.

[11] Patent Number: 5,235,038

[45] Date of Patent: Aug. 10, 1993

[54] DELETION AND SUBSTITUTION ANALOGUES OF MELITTIN PEPTIDE

[75] Inventors: Sylvie E. Blondelle, La Jolla; Richard A. Houghten, Solana Beach, both of Calif.

[73] Assignee: Torry Pines Institute for Molecular Studies, San Diego, Calif.

[21] Appl. No.: 643,343

[22] Filed: Jan. 22, 1991

[51] Int. Cl.⁵ .................. A61K 37/02; C07K 7/10
[52] U.S. Cl. .................. 530/324; 530/325; 530/326; 530/858
[58] Field of Search .......... 514/12, 13; 530/324, 530/325, 326, 858; 930/190, DIG. 821

[56] References Cited

U.S. PATENT DOCUMENTS

| | | | |
|---|---|---|---|
| 4,810,777 | 3/1989 | Zasloff | 930/190 |
| 4,822,608 | 4/1989 | Benton et al. | 514/12 |
| 4,962,277 | 10/1990 | Cuervo et al. | 530/326 |

FOREIGN PATENT DOCUMENTS 4371 5/1989 World Int. Prop. O. .

OTHER PUBLICATIONS

Dayhoff, *Atlas of Protein Sequence and Structure 1972* vol. 5, Nat. Biomed. Res. Found, p. 96.
Kreil, "The Structure of Apis Dorsata Melittin: Phylogenetic Relationships between Honeybees . . . ", *FEBS Lett.* 54(1), Jun. 1975, pp. 100–102.
Wade et al, "All-amino acid-containing channel-forming antibiotic peptides," *PNAS USA* 87, Jun. 1990, pp. 4761–4765.

*Primary Examiner*—Jeffrey E. Russel
*Attorney, Agent, or Firm*—Elliot M. Olstein; Raymond J. Lillie

[57] ABSTRACT

A compound comprising an analogue of the melittin peptide having the following structural formula:

(SEQ ID NO: 1)

| Gly | Ile | Gly | Ala | Val | Leu | Lys | Val | Leu |
|---|---|---|---|---|---|---|---|---|
| 1 | 2 | 3 | 4 | 5 | 6 | 7 | 8 | 9 |
| Thr | Thr | Gly | Leu | Pro | Ala | Leu | Ile | Ser |
| 10 | 11 | 12 | 13 | 14 | 15 | 16 | 17 | 18 |
| Trp | Ile | Lys | Arg | Lys | Arg | Gln | Gln | |
| 19 | 20 | 21 | 22 | 23 | 24 | 25 | 26, | | wherein at least one and no more than four amino acid residues are omitted from the peptide, or at least one of amino acid residues 1–6, 8–18, or 20–26 in the peptide is substituted with a hydrophobic residue, provided that no more than two of amino acid residues 21–26 is substituted with a hydrophobic residue. Such deletion and substitution analogues are useful as antibiotics, antimicrobial agents, antifungal agents, anti-tumor agents, antiviral agents, or agents which stimulate wound healing.

6 Claims, No Drawings

DELETION AND SUBSTITUTION ANALOGUES OF MELITTIN PEPTIDE

This invention relates to analogues of the peptide known as melittin. More particularly, this invention relates to analogues of melittin peptide wherein an amino acid residue(s) is omitted or substituted.

Melittin is an amphipathic peptide consisting of 26 amino acid residues, and is isolated from honeybee (Apis mellifera) venom. The peptide is known to be cytolytic. Habermann, et al., *Hoppe-Sevler's Zeitschrift Physiol. Chem.*, Vol. 348, pgs. 37–50 (1987). Melittin has the following structural formula as represented by the three-letter amino acid code:

```
                                          (SEQ ID NO: 1)
Gly  Ile  Gly  Ala  Val  Leu  Lys  Val  Leu
                     5
Thr  Thr  Gly  Leu  Pro  Ala  Leu  Ile  Ser
10                      15
Trp  Ile  Lys  Arg  Lys  Arg  Gln  Gln
     20                    25
```

In accordance with an aspect of the present invention, there is provided a compound comprising a deletion analogue of an amide- or carboxy-terminated melittin peptide wherein the melittin peptide is represented by the following structural formula using the three-letter amino acid code and the numbers below each amino acid residue refer to the position of the residue in the peptide:

| Gly | Ile | Gly | Ala | Val | Leu | Lys | Val | Leu | Thr | Thr | Gly | Leu | Pro | Ala | Leu | (SEQ ID NO: 1) |
|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | |
| Ile | Ser | Trp | Ile | Lys | Arg | Lys | Arg | Gln | Gln | | | | | | | |
| 17 | 18 | 19 | 20 | 21 | 22 | 23 | 24 | 25 | 26 | | | | | | | |

At least one and no more than four of the amino acid residues 1 through 26 is omitted from the peptide.

In accordance with one embodiment, one of amino acid residues 1 through 26 is omitted from the peptide. In a preferred embodiment, one of amino acid residues, 1, 10, 11, 12, 21, 24, 25, or 26 is omitted from the peptide. Most preferably, amino acid residue 12 is omitted from the peptide.

Representative examples of such deletion analogues have the following structural formulae as listed in the accompanying sequence listing:

(a) SEQ ID NO: 2 (residue 1 omitted);
(b) SEQ ID NO: 3 (residue 2 omitted);
(c) SEQ ID NO: 4 (residue 3 omitted);
(d) SEQ ID NO: 5 (residue 4 omitted);
(e) SEQ ID NO: 6 (residue 5 omitted);
(f) SEQ ID NO: 7 (residue 6 omitted);
(g) SEQ ID NO: 8 (residue 7 omitted);
(h) SEQ ID NO: 9 (residue 8 omitted);
(i) SEQ ID NO: 10 (residue 9 omitted);
(j) SEQ ID NO: 11 (residue 10 or 11 omitted);
(k) SEQ ID NO: 12 (residue 12 omitted);
(l) SEQ ID NO: 13 (residue 13 omitted);

-continued (m) SEQ ID NO: 14 (residue 14 omitted);
(n) SEQ ID NO: 15 (residue 15 omitted);
(o) SEQ ID NO: 16 (residue 16 omitted);
(p) SEQ ID NO: 17 (residue 17 omitted);
(q) SEQ ID NO: 18 (residue 18 omitted);
(r) SEQ ID NO: 19 (residue 19 omitted);
(s) SEQ ID NO: 20 (residue 20 omitted);
(t) SEQ ID NO: 21 (residue 21 omitted);
(u) SEQ ID NO: 22 (residue 22 omitted);
(v) SEQ ID NO: 23 (residue 23 omitted);
(w) SEQ ID NO: 24 (residue 24 omitted);
(x) SEQ ID NO: 25 (residue 25 or 26 omitted).

In accordance with another aspect of the present invention, there is provided a substitution analogue of an amide- or carboxy-terminated melittin peptide. The melittin peptide has the same structural formula (SEQ ID NO: 1) as hereinabove described. At least one of amino acid residues 1–6, 8–18, or 20–26 is substituted with a hydrophobic residue, said hydrophobic residue being different from the amino acid residue normally present in the melittin peptide, and provided that no more than two of amino acid residues 21–26 are substituted with a hydrophobic residue.

The hydrophobic amino acids are Ala, Cys, Gly, Ile, Leu, Met, Phe, Pro, Trp, Tyr, Val, norleucine (Nle), norvaline (Nva), and cyclohexylalanine (Cha).

The neutral hydrophilic amino acids are Asn, Gln, Ser, and Thr.

The basic hydrophilic amino acids are Lys, Arg, His, and Orn.

The acidic hydrophilic amino acids are Asp and Glu.

In a preferred embodiment, at least one and no more than ten of amino acid residues 1–5, 8, 10–12, 14, 15, 17, 18, or 20–26 is substituted with a leucine residue, provided that no more than two of amino acid residues 21–26 is substituted with a leucine residue. In accordance with one embodiment, one of amino acid residues 1–5, 8, 10–12, 14, 15, 17, 18, or 20–26 is substituted with a leucine residue.

Representative examples of such substitution analogues, wherein one amino acid residue has been substituted with a leucine residue, have the following structural formulae as listed in the accompanying sequence listing:

(a) SEQ ID NO: 26 (residue 1 substituted);
(b) SEQ ID NO: 27 (residue 2 substituted);
(c) SEQ ID NO: 28 (residue 3 substituted);
(d) SEQ ID NO: 29 (residue 4 substituted);
(e) SEQ ID NO: 30 (residue 5 substituted);
(f) SEQ ID NO: 31 (residue 8 substituted);
(g) SEQ ID NO: 32 (residue 10 substituted);
(h) SEQ ID NO: 33 (residue 11 substituted);
(i) SEQ ID NO: 34 (residue 12 substituted);
(j) SEQ ID NO: 35 (residue 14 substituted);
(k) SEQ ID NO: 36 (residue 15 substituted);
(l) SEQ ID NO: 37 (residue 17 substituted);
(m) SEQ ID NO: 38 (residue 18 substituted);
(n) SEQ ID NO: 39 (residue 20 substituted);
(o) SEQ ID NO: 40 (residue 21 substituted);
(p) SEQ ID NO: 41 (residue 22 substituted);
(q) SEQ ID NO: 42 (residue 23 substituted);
(r) SEQ ID NO: 43 (residue 24 substituted);
(s) SEQ ID NO: 44 (residue 25 substituted);

| | |
|---|---|
| (t) | SEQ ID NO: 45 (residue 26 substituted); |

In general, the peptides hereinabove described are generally water soluble to a concentration of at least 20 mg/ml at neutral pH in water. In addition, the structure of such peptide provides for flexibility of the peptide molecule. When the peptide is placed in water, it does not assume an amphiphilic structure.

The peptides and/or analogues or derivatives thereof may be administered to a host; for example a human or non-human animal, in an amount effective to inhibit growth of a target cell, virus, or virally-infected cell. Thus, for example, the peptides and/or analogues or derivatives thereof may be used an antimicrobial agents, anti-viral agents, antibiotics, anti-tumor agents, antiparasitic agents, antifungal agents, spermicides, as well as exhibiting other bioactive functions.

The term "antimicrobial" as used herein means that the peptides of the present invention inhibit, prevent, or destroy the growth or proliferation of microbes such as bacteria, fungi, or the like.

The term "antibiotic" as used herein means that the peptides employed in the present invention produce effects adverse to the normal biological functions of the non-host cell, tissue or organism, including death or destruction and prevention of the growth or proliferation of the non-host cell, tissue, or organism, when contacted with the peptides.

The term "spermicidal" as used herein means that the peptides employed in the present invention inhibit, prevent, or destroy the motility of sperm.

The term "antiviral" as used herein means that the peptides employed in the present invention inhibit, prevent, or destroy the growth or proliferation of viruses, or of virally-infected cells.

The term "anti-tumor" as used herein means that the peptide inhibits the growth of or destroys tumors.

The term "antifungal" as used herein means that the peptides of the present invention may be used to inhibit the growth of or destroy fungi.

The term "antiparasitic" as used herein means that the peptides of the present invention may be used to inhibit the growth of or destroy parasites.

The peptides may be administered in vivo or in vitro. The peptides also may be administered directly to a target cell, virus, or virally-infected cell, or the peptides may be administered systemically.

The peptides of the present invention have a broad range of potent antibiotic activity against a plurality of microorganisms including Gram-positive and Gram-negative bacteria, fungi, protozoa, and the like, as well as parasites. The peptides of the present invention allow a method for treating or controlling microbial infection caused by organisms which are sensitive to the peptides. Such treatment may comprise administering to a host organism or tissue susceptible to or affiliated with a microbial infection an antimicrobial amount of at least one of the peptides.

Because of the antibiotic, antimicrobial, and antiviral properties of the peptides, they may also be used as preservatives or sterilants of materials susceptible to microbial or viral contamination.

The peptide may be administered in combination with a non-toxic pharmaceutical carrier or vehicle such as a filler, non-toxic buffer, or physiological saline solution. Such pharmaceutical compositions may be used topically or systemically and may be in any suitable form such as a liquid, solid, semi-solid, injectable solution, tablet, ointment, lotion, paste, capsule, or the like. The peptide compositions may also be used in combination with adjuvants, protease inhibitors, or compatible drugs where such a combination is seen to be desirable or advantageous in controlling infection caused by harmful microorganisms including protozoa, viruses, and the like, as well as by parasites.

The peptide(s) of the present invention may be administered to a host; in particular an animal, in an effective antibiotic and/or anti-tumor and/or anti-viral and/or anti-microbial and/or anti-parasitic and/or an antispermicidal amount.

Depending on the use, a composition in accordance with the invention will contain an effective antimicrobial amount and/or an effective antispermicidal amount and/or an effective antiviral amount and/or an effective anti-tumor amount and/or an effective antibiotic amount and/or antiparasitic amount of one or more of the hereinabove described peptides which have such activity.

The peptide of the present invention may also be employed in promoting or stimulating healing of a wound in a host.

The term "wound healing" as used herein includes various aspects of the wound healing process.

These aspects include, but are not limited to, increased contraction of the wound, increased deposition of connective tissue, as evidenced by, for example, increased deposition of collagen in the wound, and increased tensile strength of the wound, i.e., the peptides increase wound breaking strength. The peptides of the present invention may also be employed so as to reverse the inhibition of wound healing caused by conditions which compromise or depress the immune system.

The peptides of the present invention may be used in the treatment of external burns and to treat and/or prevent skin and burn infections. In particular, the peptides may be used to treat skin and burn infections caused by organisms such as, but not limited to, P. aeruginosa and S. aureus.

The peptides are also useful in the prevention or treatment of eye infections. Such infections may be caused by bacteria such as, but not limited to, P. aeruginosa, S. aureus, and N. gonorrhoeae, by fungi such as but not limited to C. albicans and A. fumigatus, by parasites such as but not limited to A. castellani, or by viruses.

The peptides may also be effective in killing cysts, spores, or trophozoites of infection - causing organisms. Such organisms include, but are not limited to Acanthamoeba which forms trophozoites or cysts, C. albicans, which forms spores, and A. fumigatus, which forms spores as well.

The peptides may also be administered to plants in an effective antimicrobial or antiviral or antiparasitic amount to prevent or treat microbial or viral or parasitic contamination thereof.

In general, the peptide is employed to provide peptide dosages of from 0.1 mg. to 500 mg. per kilogram of host weight. When administered topically, the peptide is used in a concentration of from 0.05% to 10%.

The invention will now be described with respect to the following examples; however, the scope of the present invention is not intended to be limited thereby.

EXAMPLE 1

Peptide Synthesis

The deletion analogues, wherein one of the amino acids is omitted from the melittin peptide (SEQ ID. NO: 1) hereinabove described, were synthesized by simultaneous multiple peptide synthesis (SMPS) as disclosed in Houghten, *Proc. Natl. Acad. Sci.*, Vol. 82, pgs. 5131-5135 (1985).

Protected t-Boc amino acids were obtained from Bachem Inc. and used as received. The side chains of serine and threonine were protected with O-benzyl groups, lysine with o-chlorobenzyloxy-carbonyl, arginine with tosyl and tryptophan with formyl. SMPS was performed using 100 mg of p-methyl benzhydrylamine resin (m-BHA) (substitution=0.54 meq/g) in each individual resin packet. To obtain omission or deletion analogs, individual packets were removed during coupling of the corresponding omitted or deleted residue to all of the other analogs and then returned to the common reaction vessel before completing the synthesis. For cleavage, Tam's low-high HF procedure was used (Tam et al., *J. Am. Chem. Soc.*, Vol. 105, pgs. 6442-6455, 1983). All of the m-BHA resins were treated in a common vessel for the low HF step since little peptide is lost from m-BHA during this step. The high HF step was performed in a 24-vessel apparatus as described in Houghten, et al., *Int. J. Pept. Protein Res.*, Vol. 27, pgs. 673-678 (1986) and available from Multiple Peptide Systems (San Diego, CA). The identities of the resulting peptides were confirmed by amino acid analysis (Yale University School of Medicine—New Haven, CT), and by Fast Atom Bombardment mass spectroscopy analyses (M-Scan Inc., West Chester, PA) and/or by Time-of-flight mass spectroscopy analyses on a BIOION 20 spectrometer.

EXAMPLE 2

Antimicrobial Assays

Each of the deletion analogues was tested for minimum inhibitory concentration (MIC) against *Pseudomonas aeruginosa* ATCC 27853 and *Staphylococcus aureus* ATCC 29213. In 96-well tissue culture plates, bacteria were grown overnight at 37° C. in Luria-Bertani (LB) medium. This culture was reinoculated and incubated at 37° C. to reach the exponential phase of bacterial growth, i.e., a final bacterial suspension containing $10^5$ to $5 \times 10^5$ colony-forming units (CFU)/ml. Melittin or one of the deletion analogues (dissolved in 1×PBS, pH7.0) was then added to each well in concentrations ranging from 1.5 µg/ml to greater than 100 µg/ml. The concentration of cells was established by plating 100 µl of different dilutions of the culture solution (e.g., $10^2$, $10^3$ and $10^4$) onto solid agar plates. Following an overnight incubation at 37° C., the CFU's thus formed were counted on each agar plate. As control blanks, eight wells per plate contained only medium, while as a positive growth control, eight other wells contained medium plus cells. These controls were used to detect possible medium contamination and to provide a measure of uninhibited growth of the microorganisms. The plates were incubated overnight at 37° C., and the OD determined at 620nm using a Titertek Multiskan apparatus. The minimum inhibitory concentration (MIC) was defined as the lowest concentration of peptide at which there was no change in OD between time 0 and 18 hours.

The MIC in µg/ml of each deletion analogue of melittin, as well as the melittin peptide wherein no amino acid residues were deleted, is given in Table I below.

TABLE I

| MIC (µg/ml) Amino Acid Residue Deleted | P. aeruginosa | S. aureus |
|---|---|---|
| None (SEQ ID NO: 1) | 50 | 25 |
| 1 (SEQ ID NO: 2) | 50 | 25 |
| 2 (SEQ ID NO: 3) | 100 | 50 |
| 3 (SEQ ID NO: 4) | 100 | 50 |
| 4 (SEQ ID NO: 5) | 100 | 100 |
| 5 (SEQ ID NO: 6) | 100 | 50 |
| 6 (SEQ ID NO: 7) | >100 | >100 |
| 7 (SEQ ID NO: 8) | >100 | >100 |
| 8 (SEQ ID NO: 9) | 100 | 50 |
| 9 (SEQ ID NO: 10) | >100 | >100 |
| 10 or 11 (SEQ ID NO: 11) | 50 | 25 |
| 12 (SEQ ID NO: 12) | 50 | 12.5 |
| 13 (SEQ ID NO: 13) | >100 | >100 |
| 14 (SEQ ID NO: 14) | 100 | 25 |
| 15 (SEQ ID NO: 15) | 100 | 25 |
| 16 (SEQ ID NO: 16) | 100 | >100 |
| 17 (SEQ ID NO: 17) | 100 | >100 |
| 18 (SEQ ID NO: 18) | 100 | 100 |
| 19 (SEQ ID NO: 19) | >100 | >100 |
| 20 (SEQ ID NO: 20) | 50 | 50 |
| 21 (SEQ ID NO: 21) | 50 | 25 |
| 22 (SEQ ID NO: 22) | 50 | 50 |
| 23 (SEQ ID NO: 23) | 50 | 50 |
| 24 (SEQ ID NO: 24) | 50 | 25 |
| 25 or 26 (SEQ ID NO: 25) | 50 | 25 |

It is to be understood however that the scope of the present invention is not to be limited to the specific embodiments described above. The invention may be practiced other than as particularly described and still be within the scope of the accompanying claims.

What is claimed is:

1. A compound comprising a peptide having the following structural formula:
SEQ ID NO:11.

2. A compound comprising a peptide having the following structural formula:
SEQ ID NO:12.

3. A compound comprising a peptide having the following structural formula:

SEQ ID NO:18.

4. A compound comprising a peptide having the following structural formula:

SEQ ID NO:21.

5. A compound comprising a peptide having the following structural formula:
SEQ ID NO:24.

6. A compound comprising a peptide having the following structural formula:
SEQ ID NO:25.

* * * * *

SEQUENCE LISTING ( 1 ) GENERAL INFORMATION:

( i i i ) NUMBER OF SEQUENCES: 45

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( v i ) ORIGINAL SOURCE:

(A) ORGANISM: Apis mellifera (vii) FEATURE:
    (A) NAME/KEY: melittin peptide (x) PUBLICATION INFORMATION:
    (A) AUTHORS: Habermann, E.
                 Jentsch, J.
    (B) TITLE: Sequenzanalyse des Melittins aus
               den tryptischen und peptischen
               Spaltstücken.
    (C) JOURNAL: Hoppe-Seyler's Zeitschrift
                 Physiol. Chem.
    (D) VOLUME: 348
    (F) PAGES: 37-50
    (G) DATE: 1987

(xi) SEQUENCE DESCRIPTION: SEQ ID NO:1:

Gly Ile Gly Ala Val Leu Lys Val Leu
                 5

Thr Thr Gly Leu Pro Ala Leu Ile Ser Trp
10                   15

Ile Lys Arg Lys Arg Gln Gln
20               25

(2) INFORMATION FOR SEQ ID NO:2:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (vii) FEATURE:
        (A) NAME/KEY: deletion analogue of melittin peptide (xi) SEQUENCE DESCRIPTION: SEQ ID NO:2:

Ile Gly Ala Val Leu Lys Val Leu Thr Thr
             5           10

Gly Leu Pro Ala Leu Ile Ser Trp Ile Lys
                 15          20

Arg Lys Arg Gln Gln
                25

(2) INFORMATION FOR SEQ ID NO:3:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (vii) FEATURE:
        (A) NAME/KEY: deletion analogue of melittin peptide (xi) SEQUENCE DESCRIPTION: SEQ ID NO:3:

Gly Gly Ala Val Leu Lys Val Leu Thr Thr
             5           10

Gly Leu Pro Ala Leu Ile Ser Trp Ile Lys
                 15          20

Arg Lys Arg Gln Gln
                25

(2) INFORMATION FOR SEQ ID NO:4:

(i) SEQUENCE CHARACTERISTICS:

(A) LENGTH: 25 amino acids
(B) TYPE: amino acid
(C) STRANDEDNESS:
(D) TOPOLOGY: linear (ii) MOLECULE TYPE: peptide (vii) FEATURE:
(A) NAME/KEY: deletion analogue of melittin peptide (xi) SEQUENCE DESCRIPTION: SEQ ID NO:4:

Gly Ile Ala Val Leu Lys Val Leu Thr Thr
                  5                  10
Gly Leu Pro Ala Leu Ile Ser Trp Ile Lys
                 15                  20
Arg Lys Arg Gln Gln
                 25

(2) INFORMATION FOR SEQ ID NO:5:

(i) SEQUENCE CHARACTERISTICS:
(A) LENGTH: 25 amino acids
(B) TYPE: amino acid
(C) STRANDEDNESS:
(D) TOPOLOGY: linear (ii) MOLECULE TYPE: peptide (vii) FEATURE:
(A) NAME/KEY: deletion analogue of melittin peptide (xi) SEQUENCE DESCRIPTION: SEQ ID NO:5:

Gly Ile Gly Val Leu Lys Val Leu Thr Thr
                  5                  10
Gly Leu Pro Ala Leu Ile Ser Trp Ile Lys
                 15                  20
Arg Lys Arg Gln Gln
                 25

(2) INFORMATION FOR SEQ ID NO:6:

(i) SEQUENCE CHARACTERISTICS:
(A) LENGTH: 25 amino acids
(B) TYPE: amino acid
(C) STRANDEDNESS:
(D) TOPOLOGY: linear (ii) MOLECULE TYPE: peptide (vii) FEATURE:
(A) NAME/KEY: deletion analogue of melittin peptide (xi) SEQUENCE DESCRIPTION: SEQ ID NO:6:

Gly Ile Gly Ala Leu Lys Val Leu Thr Thr
                  5                  10
Gly Leu Pro Ala Leu Ile Ser Trp Ile Lys
                 15                  20
Arg Lys Arg Gln Gln
                 25

(2) INFORMATION FOR SEQ ID NO:7:
(i) SEQUENCE CHARACTERISTICS:
(A) LENGTH: 25 amino acids
(B) TYPE: amino acid
(C) STRANDEDNESS:
(D) TOPOLOGY: linear (ii) MOLECULE TYPE: peptide (vii) FEATURE:

(A) NAME/KEY: deletion analogue of melittin peptide (xi) SEQUENCE DESCRIPTION: SEQ ID NO:7:

Gly Ile Gly Ala Val Lys Val Leu Thr Thr
                  5           10
Gly Leu Pro Ala Leu Ile Ser Trp Ile Lys
                 15          20
Arg Lys Arg Gln Gln
                25

(2) INFORMATION FOR SEQ ID NO:8:

(i) SEQUENCE CHARACTERISTICS:
      (A) LENGTH: 25 amino acids
      (B) TYPE: amino acid
      (C) STRANDEDNESS:
      (D) TOPOLOGY: linear (ii) MOLECULE TYPE: peptide (vii) FEATURE:
      (A) NAME/KEY: deletion analogue of melittin peptide (xi) SEQUENCE DESCRIPTION: SEQ ID NO:8:

Gly Ile Gly Ala Val Leu Val Leu Thr Thr
                  5           10
Gly Leu Pro Ala Leu Ile Ser Trp Ile Lys
                 15          20
Arg Lys Arg Gln Gln
                25

(2) INFORMATION FOR SEQ ID NO:9:

(i) SEQUENCE CHARACTERISTICS:
      (A) LENGTH: 25 amino acids
      (B) TYPE: amino acid
      (C) STRANDEDNESS:
      (D) TOPOLOGY: linear (ii) MOLECULE TYPE: peptide (vii) FEATURE:
      (A) NAME/KEY: deletion analogue of melittin peptide (xi) SEQUENCE DESCRIPTION: SEQ ID NO:9:

Gly Ile Gly Ala Val Leu Lys Leu Thr Thr
                  5           10
Gly Leu Pro Ala Leu Ile Ser Trp Ile Lys
                 15          20
Arg Lys Arg Gln Gln
                25

(2) INFORMATION FOR SEQ ID NO:10:

(i) SEQUENCE CHARACTERISTICS:
      (A) LENGTH: 25 amino acids
      (B) TYPE: amino acid
      (C) STRANDEDNESS:
      (D) TOPOLOGY: linear (ii) MOLECULE TYPE: peptide (vii) FEATURE:
      (A) NAME/KEY: deletion analogue of melittin peptide (xi) SEQUENCE DESCRIPTION: SEQ ID NO:10:

Gly Ile Gly Ala Val Leu Lys Val Thr Thr
                  5           10

Gly Leu Pro Ala Leu Ile Ser Trp Ile Lys
                15          20

Arg Lys Arg Gln Gln
                25

( 2 ) INFORMATION FOR SEQ ID NO:11:
    ( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:11:

Gly Ile Gly Ala Val Leu Lys Val Leu Thr
                5           10

Gly Leu Pro Ala Leu Ile Ser Trp Ile Lys
                15          20

Arg Lys Arg Gln Gln
                25

( 2 ) INFORMATION FOR SEQ ID NO:12:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:12:

Gly Ile Gly Ala Val Leu Lys Val Leu Thr
                5           10

Thr Leu Pro Ala Leu Ile Ser Trp Ile Lys
                15          20

Arg Lys Arg Gln Gln
                25

( 2 ) INFORMATION FOR SEQ ID NO:13:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:13:

Gly Ile Gly Ala Val Leu Lys Val Leu Thr
                5           10

Thr Gly Pro Ala Leu Ile Ser Trp Ile Lys
                15          20

Arg Lys Arg Gln Gln
                25

( 2 ) INFORMATION FOR SEQ ID NO:14:

(i) SEQUENCE CHARACTERISTICS:
    (A) LENGTH: 25 amino acids
    (B) TYPE: amino acid
    (C) STRANDEDNESS:
    (D) TOPOLOGY: linear (ii) MOLECULE TYPE: peptide (vii) FEATURE:
    (A) NAME/KEY: deletion analogue of melittin peptide (xi) SEQUENCE DESCRIPTION: SEQ ID NO:14:

Gly Ile Gly Ala Val Leu Lys Val Leu Thr
                 5           10

Thr Gly Leu Ala Leu Ile Ser Trp Ile Lys
                15          20

Arg Lys Arg Gln Gln
                25

(2) INFORMATION FOR SEQ ID NO:15:

(i) SEQUENCE CHARACTERISTICS:
    (A) LENGTH: 25 amino acids
    (B) TYPE: amino acid
    (C) STRANDEDNESS:
    (D) TOPOLOGY: linear (ii) MOLECULE TYPE: peptide (vii) FEATURE:
    (A) NAME/KEY: deletion analogue of melittin peptide (xi) SEQUENCE DESCRIPTION: SEQ ID NO:15:

Gly Ile Gly Ala Val Leu Lys Val Leu Thr
                 5           10

Thr Gly Leu Pro Leu Ile Ser Trp Ile Lys
                15          20

Arg Lys Arg Gln Gln
                25

(2) INFORMATION FOR SEQ ID NO:16:

(i) SEQUENCE CHARACTERISTICS:
    (A) LENGTH: 25 amino acids
    (B) TYPE: amino acid
    (C) STRANDEDNESS:
    (D) TOPOLOGY: linear (ii) MOLECULE TYPE: peptide (vii) FEATURE:
    (A) NAME/KEY: deletion analogue of melittin peptide (xi) SEQUENCE DESCRIPTION: SEQ ID NO:16:

Gly Ile Gly Ala Val Leu Lys Val Leu Thr
                 5           10

Thr Gly Leu Pro Ala Ile Ser Trp Ile Lys
                15          20

Arg Lys Arg Gln Gln
                25

(2) INFORMATION FOR SEQ ID NO:17:
    (i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide ( v i i ) FEATURE:
	( A ) NAME/KEY: deletion analogue of melittin peptide ( x i ) SEQUENCE DESCRIPTION: SEQ ID NO:17:

Gly Ile Gly Ala Val Leu Lys Val Leu Thr
					5			10

Thr Gly Leu Pro Ala Leu Ser Trp Ile Lys
					15			20

Arg Lys Arg Gln Gln
					25

( 2 ) INFORMATION FOR SEQ ID NO:18:

( i ) SEQUENCE CHARACTERISTICS:
		( A ) LENGTH: 25 amino acids
		( B ) TYPE: amino acid
		( C ) STRANDEDNESS:
		( D ) TOPOLOGY: linear ( i i ) MOLECULE TYPE: peptide ( v i i ) FEATURE:
		( A ) NAME/KEY: deletion analogue of melittin peptide ( x i ) SEQUENCE DESCRIPTION: SEQ ID NO:18:

Gly Ile Gly Ala Val Leu Lys Val Leu Thr
					5			10

Thr Gly Leu Pro Ala Leu Ile Trp Ile Lys
					15			20

Arg Lys Arg Gln Gln
					25

( 2 ) INFORMATION FOR SEQ ID NO:19:

( i ) SEQUENCE CHARACTERISTICS:
		( A ) LENGTH: 25 amino acids
		( B ) TYPE: amino acid
		( C ) STRANDEDNESS:
		( D ) TOPOLOGY: linear ( i i ) MOLECULE TYPE: peptide ( v i i ) FEATURE:
		( A ) NAME/KEY: deletion analogue of melittin peptide ( x i ) SEQUENCE DESCRIPTION: SEQ ID NO:19:

Gly Ile Gly Ala Val Leu Lys Val Leu Thr
					5			10

Thr Gly Leu Pro Ala Leu Ile Ser Ile Lys
					15			20

Arg Lys Arg Gln Gln
					25

( 2 ) INFORMATION FOR SEQ ID NO:20:

( i ) SEQUENCE CHARACTERISTICS:
		( A ) LENGTH: 25 amino acids
		( B ) TYPE: amino acid
		( C ) STRANDEDNESS:
		( D ) TOPOLOGY: linear ( i i ) MOLECULE TYPE: peptide ( v i i ) FEATURE:
		( A ) NAME/KEY: deletion analogue of melittin peptide ( x i ) SEQUENCE DESCRIPTION: SEQ ID NO:20:

Gly Ile Gly Ala Val Leu Lys Val Leu Thr

```
                         5
                                      1 0
Thr  Gly  Leu  Pro  Ala  Leu  Ile  Ser  Trp  Lys
                         1 5           2 0

Arg  Lys  Arg  Gln  Gln
                    2 5
```

( 2 ) INFORMATION FOR SEQ ID NO:21:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:21:

```
Gly  Ile  Gly  Ala  Val  Leu  Lys  Val  Leu  Thr
                         5             1 0

Thr  Gly  Leu  Pro  Ala  Leu  Ile  Ser  Trp  Ile
                         1 5           2 0

Arg  Lys  Arg  Gln  Gln
                    2 5
```

( 2 ) INFORMATION FOR SEQ ID NO:22:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:22:

```
Gly  Ile  Gly  Ala  Val  Leu  Lys  Val  Leu  Thr
                         5             1 0

Thr  Gly  Leu  Pro  Ala  Leu  Ile  Ser  Trp  Ile
                         1 5           2 0

Lys  Lys  Arg  Gln  Gln
                    2 5
```

( 2 ) INFORMATION FOR SEQ ID NO:23:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:23:

```
Gly  Ile  Gly  Ala  Val  Leu  Lys  Val  Leu  Thr
                         5             1 0

Thr  Gly  Leu  Pro  Ala  Leu  Ile  Ser  Trp  Ile
                         1 5           2 0

Lys  Arg  Arg  Gln  Gln
                    2 5
```

( 2 ) INFORMATION FOR SEQ ID NO:24:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:24:

Gly Ile Gly Ala Val Leu Lys Val Leu Thr
              5               10

Thr Gly Leu Pro Ala Leu Ile Ser Trp Ile
             15            20

Lys Arg Lys Gln Gln
            25

( 2 ) INFORMATION FOR SEQ ID NO:25:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: deletion analogue of melittin peptide ( x i ) SEQUENCE DESCRIPTION: SEQ ID NO:25:

Gly Ile Gly Ala Val Leu Lys Val Leu Thr
              5               10

Thr Gly Leu Pro Ala Leu Ile Ser Trp Ile
             15            20

Lys Arg Lys Arg Gln
            25

( 2 ) INFORMATION FOR SEQ ID NO:26:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: substitution analogue of melittin
            peptide ( x i ) SEQUENCE DESCRIPTION: SEQ ID NO:26:

Leu Ile Gly Ala Val Leu Lys Val Leu Thr
              5               10

Thr Gly Leu Pro Ala Leu Ile Ser Trp Ile
             15            20

Lys Arg Lys Arg Gln Gln
            25

( 2 ) INFORMATION FOR SEQ ID NO:27:

( i ) SEQUENCE CHARACTERISTICS:
        ( A ) LENGTH: 26 amino acids
        ( B ) TYPE: amino acid (C) STRANDEDNESS:
(D) TOPOLOGY: linear (ii) MOLECULE TYPE: peptide (vii) FEATURE:
(A) NAME/KEY: substitution analogue of melittin peptide (xi) SEQUENCE DESCRIPTION: SEQ ID NO:27:

Gly Leu Gly Ala Val Leu Lys Val Leu Thr
                 5           10

Thr Gly Leu Pro Ala Leu Ile Ser Trp Ile
                 15          20

Lys Arg Lys Arg Gln Gln
                 25

(2) INFORMATION FOR SEQ ID NO:28:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: peptide (vii) FEATURE:
(A) NAME/KEY: substitution analogue of melittin peptide (xi) SEQUENCE DESCRIPTION: SEQ ID NO:28:

Gly Ile Leu Ala Val Leu Lys Val Leu Thr
                 5           10

Thr Gly Leu Pro Ala Leu Ile Ser Trp Ile
                 15          20

Lys Arg Lys Arg Gln Gln
                 25

(2) INFORMATION FOR SEQ ID NO:29:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: peptide (vii) FEATURE:
(A) NAME/KEY: substitution analogue of melittin peptide (xi) SEQUENCE DESCRIPTION: SEQ ID NO:29:

Gly Ile Gly Leu Val Leu Lys Val Leu Thr
                 5           10

Thr Gly Leu Pro Ala Leu Ile Ser Trp Ile
                 15          20

Lys Arg Lys Arg Gln Gln
                 25

(2) INFORMATION FOR SEQ ID NO:30:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: peptide ( v i i ) FEATURE:
  ( A ) NAME/KEY: substitution analogue of melittin peptide ( x i ) SEQUENCE DESCRIPTION: SEQ ID NO:30:

Gly Ile Gly Ala Leu Leu Lys Val Leu Thr
              5           10

Thr Gly Leu Pro Ala Leu Ile Ser Trp Ile
              15          20

Lys Arg Lys Arg Gln Gln
              25

( 2 ) INFORMATION FOR SEQ ID NO:31:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:31:

Gly Ile Gly Ala Val Leu Lys Leu Leu Thr
              5           10

Thr Gly Leu Pro Ala Leu Ile Ser Trp Ile
              15          20

Lys Arg Lys Arg Gln Gln
              25

( 2 ) INFORMATION FOR SEQ ID NO:32:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:32:

Gly Ile Gly Ala Val Leu Lys Val Leu Leu
              5           10

Thr Gly Leu Pro Ala Leu Ile Ser Trp Ile
              15          20

Lys Arg Lys Arg Gln Gln
              25

( 2 ) INFORMATION FOR SEQ ID NO:33:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:33:

Gly Ile Gly Ala Val Leu Lys Val Leu Thr
                 5           10

Leu Gly Leu Pro Ala Leu Ile Ser Trp Ile
                15          20

Lys Arg Lys Arg Gln Gln
                25

( 2 ) INFORMATION FOR SEQ ID NO:34:

( i ) SEQUENCE CHARACTERISTICS:
　　　　　　　　( A ) LENGTH: 26 amino acids
　　　　　　　　( B ) TYPE: amino acid
　　　　　　　　( C ) STRANDEDNESS:
　　　　　　　　( D ) TOPOLOGY: linear ( i i ) MOLECULE TYPE: peptide ( v i i ) FEATURE:
　　　　　　　　( A ) NAME/KEY: substitution analogue of melittin
　　　　　　　　　　　　　　　　peptide ( x i ) SEQUENCE DESCRIPTION: SEQ ID NO:34:

Gly Ile Gly Ala Val Leu Lys Val Leu Thr
                 5           10

Thr Leu Leu Pro Ala Leu Ile Ser Trp Ile
                15          20

Lys Arg Lys Arg Gln Gln
                25

( 2 ) INFORMATION FOR SEQ ID NO:35:
　　　　( i ) SEQUENCE CHARACTERISTICS:
　　　　　　　　( A ) LENGTH: 26 amino acids
　　　　　　　　( B ) TYPE: amino acid
　　　　　　　　( C ) STRANDEDNESS:
　　　　　　　　( D ) TOPOLOGY: linear ( i i ) MOLECULE TYPE: peptide ( v i i ) FEATURE:
　　　　　　　　( A ) NAME/KEY: substitution analogue of melittin
　　　　　　　　　　　　　　　　peptide ( x i ) SEQUENCE DESCRIPTION: SEQ ID NO:35:

Gly Ile Gly Ala Val Leu Lys Val Leu Thr
                 5           10

Thr Gly Leu Leu Ala Leu Ile Ser Trp Ile
                15          20

Lys Arg Lys Arg Gln Gln
                25

( 2 ) INFORMATION FOR SEQ ID NO:36:

( i ) SEQUENCE CHARACTERISTICS:
　　　　　　　　( A ) LENGTH: 26 amino acids
　　　　　　　　( B ) TYPE: amino acid
　　　　　　　　( C ) STRANDEDNESS:
　　　　　　　　( D ) TOPOLOGY: linear ( i i ) MOLECULE TYPE: peptide ( v i i ) FEATURE:
　　　　　　　　( A ) NAME/KEY: substitution analogue of melittin
　　　　　　　　　　　　　　　　peptide ( x i ) SEQUENCE DESCRIPTION: SEQ ID NO:36:

Gly Ile Gly Ala Val Leu Lys Val Leu Thr
                 5           10

```
Thr Gly Leu Pro Leu Leu Ile Ser Trp Ile
            15          20

Lys Arg Lys Arg Gln Gln
                25
```

( 2 ) INFORMATION FOR SEQ ID NO:37:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: substitution analogue of melittin peptide ( x i ) SEQUENCE DESCRIPTION: SEQ ID NO:37:

```
Gly Ile Gly Ala Val Leu Lys Val Leu Thr
                5           10

Thr Gly Leu Pro Ala Leu Leu Ser Trp Ile
                15          20

Lys Arg Lys Arg Gln Gln
                25
```

( 2 ) INFORMATION FOR SEQ ID NO:38:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: substitution analogue of melittin peptide ( x i ) SEQUENCE DESCRIPTION: SEQ ID NO:38:

```
Gly Ile Gly Ala Val Leu Lys Val Leu Thr
                5           10

Thr Gly Leu Pro Ala Leu Ile Leu Trp Ile
                15          20

Lys Arg Lys Arg Gln Gln
                25
```

( 2 ) INFORMATION FOR SEQ ID NO:39:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( v i i ) FEATURE:
        ( A ) NAME/KEY: substitution analogue of melittin peptide ( x i ) SEQUENCE DESCRIPTION: SEQ ID NO:39:

```
Gly Ile Gly Ala Val Leu Lys Val Leu Thr
                5           10

Thr Gly Leu Pro Ala Leu Ile Ser Trp Leu
                15          20

Lys Arg Lys Arg Gln Gln
```

( 2 ) INFORMATION FOR SEQ ID NO:40:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:40:

Gly Ile Gly Ala Val Leu Lys Val Leu Thr
                 5          10
Thr Gly Leu Pro Ala Leu Ile Ser Trp Ile
                15          20
Leu Arg Lys Arg Gln Gln
                25

( 2 ) INFORMATION FOR SEQ ID NO:41:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:41:

Gly Ile Gly Ala Val Leu Lys Val Leu Thr
                 5          10
Thr Gly Leu Pro Ala Leu Ile Ser Trp Ile
                15          20
Lys Leu Lys Arg Gln Gln
                25

( 2 ) INFORMATION FOR SEQ ID NO:42:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:42:

Gly Ile Gly Ala Val Leu Lys Val Leu Thr
                 5          10
Thr Gly Leu Pro Ala Leu Ile Ser Trp Ile
                15          20
Lys Arg Leu Arg Gln Gln
                25

( 2 ) INFORMATION FOR SEQ ID NO:43:

( i ) SEQUENCE CHARACTERISTICS:
  ( A ) LENGTH: 26 amino acids
  ( B ) TYPE: amino acid
  ( C ) STRANDEDNESS:
  ( D ) TOPOLOGY: linear ( i i ) MOLECULE TYPE: peptide ( v i i ) FEATURE:
  ( A ) NAME/KEY: substitution analogue of melittin peptide ( x i ) SEQUENCE DESCRIPTION: SEQ ID NO:43:

Gly Ile Gly Ala Val Leu Lys Val Leu Thr
             5          10

Thr Gly Leu Pro Ala Leu Ile Ser Trp Ile
             15         20

Lys Arg Lys Leu Gln Gln
             25

( 2 ) INFORMATION FOR SEQ ID NO:44:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:44:

Gly Ile Gly Ala Val Leu Lys Val Leu Thr
             5          10

Thr Gly Leu Pro Ala Leu Ile Ser Trp Ile
             15         20

Lys Arg Lys Arg Leu Gln
             25

( 2 ) INFORMATION FOR SEQ ID NO:45:

( i ) SEQUENCE CHARACTERISTICS:
    ( A ) LENGTH: 26 amino acids
    ( B ) TYPE: amino acid
    ( C ) STRANDEDNESS:
    ( D ) TOPOLOGY: linear ( i i ) MOLECULE TYPE: peptide ( v i i ) FEATURE:
    ( A ) NAME/KEY: substitution analogue of melittin peptide ( x i ) SEQUENCE DESCRIPTION: SEQ ID NO:45:

Gly Ile Gly Ala Val Leu Lys Val Leu Thr
             5          10

Thr Gly Leu Pro Ala Leu Ile Ser Trp Ile
             15         20

Lys Arg Lys Arg Gln Leu
             25